United States Patent
Eliu et al.

Patent Number: 6,031,126
Date of Patent: Feb. 29, 2000

[54] PROCESS

[75] Inventors: Victor Eliu, Lörrach, Germany; Werner Kanert, Hegenheim, France; Adriano Indolese, Möhlin, Switzerland; Philipp Wyser, Ittingen, Switzerland; Anita Schnyder, Allschwil, Switzerland

[73] Assignee: Ciba Specialty Chemicals Corporation, Tarrytown, N.Y.

[21] Appl. No.: 09/065,269

[22] Filed: Apr. 23, 1998

[30] Foreign Application Priority Data

Apr. 24, 1997 [GB] United Kingdom ............... 9708305

[51] Int. Cl.⁷ ................... C07C 303/02; C07C 69/76
[52] U.S. Cl. ................... 562/88; 562/74; 562/83; 560/14; 560/64; 560/65
[58] Field of Search ............... 592/74, 83, 88; 560/14, 64, 65

[56] References Cited

U.S. PATENT DOCUMENTS

| | | | |
|---|---|---|---|
| 3,984,399 | 10/1976 | Weber et al. ............... | 260/240 |
| 4,564,479 | 1/1986 | Spencer ............... | 260/465 |
| 5,208,376 | 5/1993 | Habig et al. ............... | 564/309 |
| 5,231,223 | 7/1993 | Bader et al. ............... | 562/87 |

FOREIGN PATENT DOCUMENTS

| | | |
|---|---|---|
| 0032784 | 7/1981 | European Pat. Off. . |
| 0508264 | 10/1992 | European Pat. Off. . |
| 9107377 | 5/1991 | WIPO . |

OTHER PUBLICATIONS

Chem. Abstr. 73:87625 for CS 133236.
Chem. Abstr. 116:105822 for HU 56535.
J. Chem. Soc., Perkin Transactions 1, No. 3, Feb. 7, 1998, p. 407–410.

Primary Examiner—Gary Geist
Assistant Examiner—Brian J. Davis
Attorney, Agent, or Firm—Kevin T. Mansfield

[57] ABSTRACT

A process for the production of a fluorescent whitening agent of formula:

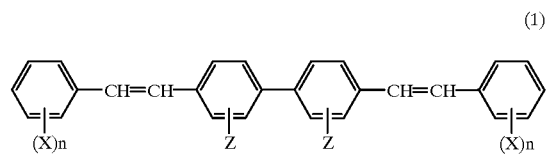

(1)

in which X and Z are as defined herein, comprising

A) rearranging a hydrazobenzene compound having the formula:

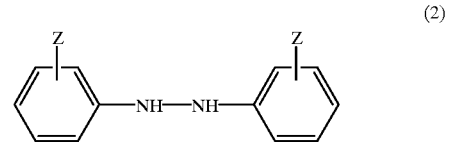

(2)

in which Z is as defined herein, to produce in situ a compound having the formula:

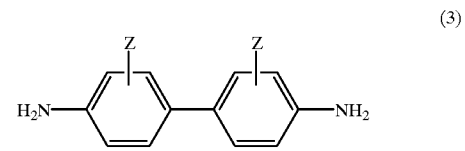

(3)

B) diazotising the compound of formula (3) to produce a compound having the formula:

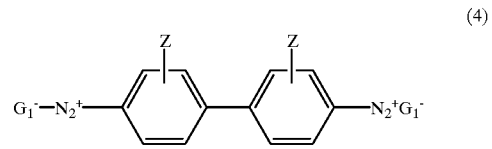

(4)

in which Z has its previous significance and $G_1$ is a counter ion; and

C) reacting the compound of formula (4) with 2 moles of a compound having the formula:

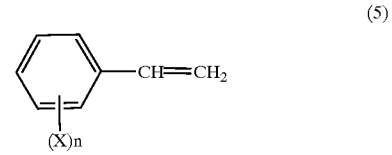

(5)

in which X and n have their previous significance, in the presence of an inorganic or organic palladium salt, or a mixture thereof, as catalyst-precursor, to produce a compound having the formula (1).

27 Claims, No Drawings

PROCESS

PROCESS

The present invention relates to a process for the production of fluorescent whitening agents and, in particular, to a process for the production of distyryl-biphenyl fluorescent whitening agents.

The compounds of formula:

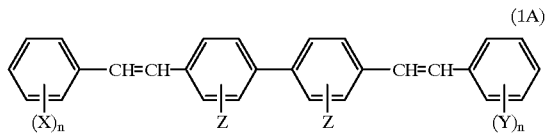
(1A)

in which X and Y, independently, are hydrogen, halogen, $NO_2$, $CF_3$, CN, $C_1$–$C_4$alkyl, $C_1$–$C_4$alkoxy, COO—$C_1$–$C_4$alkyl, CO—$C_1$–$C_4$alkyl, NH-($C_1$–$C_4$alkyl), N($C_1$–$C_4$alkyl)$_2$, NH($C_1$–$C_4$alkyl-OH), N($C_1$–$C_4$alkyl-OH)$_2$, COOH or $SO_3H$ or an ester or amide thereof, or COOM or $SO_3M$ in which M is Na, K, Ca, Mg, ammonium, mono-, di-, tri- or tetra-$C_1$–$C_4$alkylammonium, mono-, di- or tri-hydroxyalkylammonium or ammonium that is di- or tri-substituted with a mixture of $C_1$–$C_4$alkyl and $C_1$–$C_4$hydroxyalkyl groups;

Z is hydrogen, $C_1$–$C_4$alkyl, $C_1$–$C_4$alkoxy, $CF_3$, halogen, $SO_3H$ or $SO_3M$ in which M has its previous significance; and n is 1 or 2;

are known fluorescent whitening agents or are precursors therefor.

In EP-508,264, a process for the production of symmetrical compounds of formula (IA) has been described, comprising reacting a tetrazonium compound having the formula:

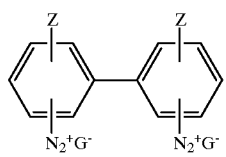

in which Z has its previous significance and G is a sulfate or bisulfate anion, with two moles of a monovinyl compound having the formula:

in which $R_1$, inter alia, is optionally substituted $C_6$–$C_{10}$aryl. The reaction is conducted in the presence of an inorganic or organic palladium salt, or a mixture thereof, as catalyst, and in water, an alcohol or a mixture thereof, as solvent.

The said tetrazonium compound reactant, however, is derived from the highly mutagenic compound benzidine.

A new route to symmetrical compounds of formula (1A) has now been found which uses safe starting materials and which provides high yields of the end products.

Accordingly, the present invention provides a process for the production of a compound of formula:

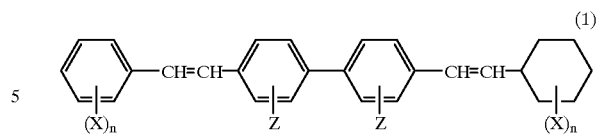
(1)

in which X is hydrogen, halogen, $NO_2$, $CF_3$, CN, $C_1$–$C_4$alkyl, $C_1$–$C_4$alkoxy, COO—$C_1$–$C_4$alkyl, CO—$C_1$–$C_4$alkyl, NH-($C_1$–$C_4$alkyl), N($C_1$–$C_4$alkyl)$_2$, NH($C_1$–$C_4$alkyl-OH), N($C_1$–$C_4$alkyl-OH)$_2$, COOH or $SO_3H$ or an ester or amide thereof, or COOM or $SO_3M$ in which M is Na, K, Ca, Mg, ammonium, mono-, di-, tri- or tetra-$C_1$–$C_4$alkylammonium, mono-, di- or tri-hydroxyalkylammonium or ammonium that is di- or tri-substituted with a mixture of $C_1$–$C_4$alkyl and $C_1$–$C_4$hydroxyalkyl groups;

Z is hydrogen, $C_1$–$C_4$alkyl, $C_1$–$C_4$alkoxy, $CF_3$, halogen (F, Cl, Br, I), $SO_3H$ or $SO_3M$ in which M has its previous significance; and n is 1 or 2; comprising A) rearranging a hydrazobenzene compound having the formula:

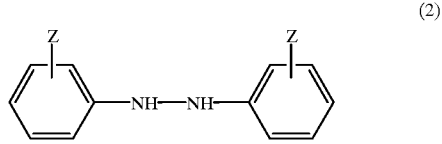
(2)

in which Z has its previous significance, to produce in situ a compound having the formula:

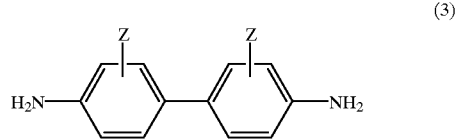
(3)

B) diazotising the compound of formula (3) to produce a compound having the formula:

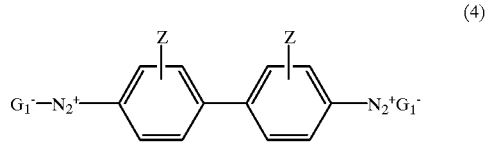
(4)

in which Z has its previous significance and $G_1$ is a counter ion; and

C) reacting the compound of formula (4) with 2 moles of a compound having the formula:

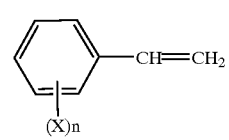
(5)

in which X and n have their previous significance, in the presence of an inorganic or organic palladium salt, or a mixture thereof, as catalyst-precursor, to produce a compound having the formula (1).

It is advantageous to conduct step C) of the process without the intermediate isolation of the reactant of formula (4) obtained in step B).

In the compounds of formula (1) and (5), preferably n is 1 and X is hydrogen, cyano, COOM or $SO_3M$ in which M has its previous significance, and in the compounds of formula (1), (2), (3) and (4), preferably Z is hydrogen.

In the compounds of formula (4), preferably $G_1$ is $H_2PO_4^-$, $HPO_4^{2-}$, $NO_3^-$, $CF_3COO^-$, $^-OOC-COO^-$ (oxalate), $Cl_3CCOO^-$, $ClCH_2COO^-$, $I^-$, $Cl^-$, $Br^-$, $F^-$, $ClO_4^-$, $PF_6^-$, $BF_4^-$, $Oac^-$, $HSO_4^-$, $SO_4^{2-}$, $CH_3(C_6H_4)SO_3^-$ or $CH_3SO_3^-$, especially $H_2PO_4^-$, $Cl_3CCOO^-$, $ClCH_2COO^-$, $PF_6^-$, $BF_4^-$, $Oac^-$, $HSO_4^-$, $SO_4^{2-}$, $CH_3(C_6H_4)SO_3^-$ or $CH_3SO_3^-$.

The diazonium compounds having the formula (4) are known compounds and the diazonium reaction of step B) may be conducted by methods known per se. The diazonium compounds are formed in situ. The in situ formation may also be conducted in the presence of the olefins of formula $CHR_2=CHR_3$ in which $R_2$ is H, F, Cl, Br or $-COOR_4$ (in which $R_4$ is H or $C_1-C_4$alkyl) and $R_3$ is $-COO$ ($C_1-C_4$alkyl), $-COR_4$ or $C_1-C_2$alkyl optionally substituted by halogen, e.g. by the addition of alkyl nitrites such as t-butyl nitrite, as described in J. Org. Chem. vol.46, pp. 4885–4888 (1981).

For example, the said diazonium compounds may be produced by reacting the corresponding amines with an alkali metal nitrite, an alkyl nitrite or nitrosylsulfonic acid, optionally in the presence of an acid, in aqueous or in organic solution. If the diazotisation is conducted in organic solution, it is preferred that the water, produced as a by-product of the diazotisation reaction, is removed either as it is formed, or prior to the reaction step C). The removal of such water may be conveniently conducted by effecting the diazotisation in the presence of water-binding materials such as acetic anhydride, sodium sulfate, calcium chloride or molecular sieves.

The reactants of formula (5) used in step C) are known compounds. They are preferably produced by reacting a diazonium compound having the formula:

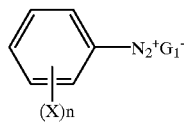

(6)

in which X, n and $G_1$ have their previous significance, with ethylene in the presence of an inorganic or organic palladium salt, or a mixture thereof, as catalyst-precursor, to produce a compound having the formula (5).

When n is 1, examples of the amino component precursors of the diazo salt starting materials of formula (6) include, e.g., aniline, 2-, 3- or 4-chloro-aniline, 2-, 3- or 4-bromo-aniline, 2-, 3- or 4iodo-aniline, 2-, 3- or 4-trifluoromethyl-aniline, 2-, 3- or 4-nitrilo-aniline, 2-3- or 4-methyl-aniline, 2-, 3- or 4-ethyl-aniline, 2-, 3- or 4-n-propyl-aniline, 2-, 3- or 4-n-butyl-aniline, 2-, 3- or 4-methoxy-aniline, 2-, 3- or 4-ethoxy-aniline, 2-, 3- or 4-n-propoxy-aniline, 2-, 3-or 4-n-butoxy-aniline, 2-, 3- or 4-amino-benzoic acid or its methyl, -ethyl-, n-propyl or n-butyl ester, 2-, 3- or 4-amino-acetophenone, 2-, 3- or 4-methylamino-aniline, 2-, 3- or 4-ethylamino-aniline, 2-, 3- or 4-hydroxyethyleneamino-aniline, 2-, 3- or 4-di (hydroxyethyleneamino)-aniline and 2-, 3- or 4-aminobenzene sulfonic acid. In the cases of 2-, 3- or 4-aminobenzoic acid and 2-, 3- or 4-aminobenzene sulfonic acid, these acids may be used in the form of their respective salts in which the cation M has its previous significance and is preferably sodium.

When n is 2, examples of the amino component precursors of the diazo salt starting materials of formula (6) include, e.g., 3- or 4-aminobenzo-1,2-dinitrile, 3- or 4-aminobenzene-1,2-dicarboxylic acid or its dimethyl, -diethyl-, di-n-propyl or di-n-butyl ester, iaminobenzene-2,4-disulfonic acid, aminobenzene-3,5-disulfonic acid or aminobenzene-2,5 disulfonic acid. In the cases of 3- or 4-aminobenzene-1,2-dicarboxylic acid and aminobenzene-2,4-disulfonic acid, aminobenzene-3,5-disulfonic acid or aminobenzene2,5-disulfonic acid, these acids may be used in the form of their respective salts in which the cation M has its previous significance and is preferably sodium.

The preferred amino component precursor of the diazonium compound of formula (6) is 2-, 3- or 4-aminobenzene sulfonic acid.

The preferred product of the process of the present invention has the formula:

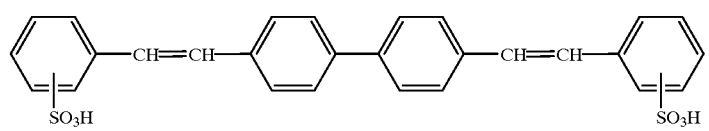

(101)

or an alkali metal salt, especially the sodium salt thereof.

The palladium catalyst precursor, used in step C) and in the production of the compounds of formula (6), may be generated, in situ or ex situ, by reduction of a palladium (II) compound, optionally in the presence of a salt such as sodium acetate, and optionally in the presence of suitable ligand-forming or colloid-stabilising compounds. Suitable palladium (II) compounds include $PdCl_2$, $PdBr_2$, $Pd(NO_3)_2$, $H_2PdCl_4$, $Pd(OOCCH_3)_2$, $[PdCl_4]Na_2$, $[PdCl_4]Li_2$, $[PdCl_4]K_2$, palladium(II)acetylacetonate, dichloro-(1,5-cyclooctadiene)palladium(II), dichlorobis-(acetonitrile)palladium(II), dichlorobis-(benzonitrile)palladium(II), π-allylpalladium(II)chloride dimer, bis-(π-methallyl palladium(ll)chloride) and π-allylpalladium(II) acetylacetonate. Suitable ligand-forming compounds are, for example, olefins having the formula $CHR_2=CHR_3$ in which $R_2$ is H, F, Cl, Br or $-COOR_4$ (in which $R_4$ is H or $C_1-C_4$alkyl) and $R_3$ is $-COO(C_1-C_4$alkyl), $-COR_4$ or $C_1-C_2$alkyl optionally substituted by halogen; dibenzylideneacetone (dba) optionally substituted with halogen (F, Cl or Br), $SO_3M$ (in which M has its previous significance), $C_1-C_4$alkyl or $C_1-C_4$alkoxy in the benzene rings; phosphites such as those of formula $P(OR_5)$ in which $R_5$ is e.g. phenyl, $C_1-C_6$alkyl or a partially or perfluorinated $C_1-C_6$alkyl; or CO. The substituents in the benzene rings are preferably linked in the para-positions of the benzene rings. The ligand-forming compounds may be used alone or in combinations of at least two compounds. The production of the palladium catalyst precursor used in step C) and in the production of the compounds of formula (6) is described in more detail in EP-564,043.

Suitable reducing agents are, e.g., CO, $H_2$, formates, primary or secondary $C_1$–$C_8$alkanols, hydrazine, amines, mixtures of CO with alkanols or water, or the ligating olefine per se.

The catalyst may be added as $Pd(dba)_2$, $Pd(dba)_3$.solvent $Pd_2(dba)_3$ or $Pd_2(dba)_3$.solvent. The dba ligand may be optionally substituted in the aromatic part as described above. Optionally, the catalyst may be added as Pd on a suitable support such as charcoal or $Al_2O_3$ (EP-606,058).

Preferably the palladium catalyst is used in an amount of 0.01 to 5 mole %, based on the diazonium salt of formula (2) or the styrene compound of formula (3).

After completion of the process according to the present invention, the palladium catalyst is preferably recovered for re-use, by methods which are well-known.

Step C) of the process according to the present invention and the production of the compounds of formula (6) may be effected in water, as solvent, in which case, preferably the palladium compound catalyst used contains one or more water-solubilising groups such as sulfo groups or carboxyl groups.

If desired, step C) of the process according to the present invention and the production of the compounds of formula (6) may be conducted in a two-phase solvent system comprising water and a water-insoluble organic solvent, such as halogenated hydrocarbon, e.g. dichloromethane, or a $C_5$–$C_{12}$alcohol such as n-pentanol. In such two-phase reaction systems, optionally a phase transfer catalyst or a suitable surfactant may be present.

Preferably, however, step C) of the process according to the present invention and the production of the compounds of formula (6) are conducted in an organic solvent, preferably in one or more of the following: alcohols; ketones; carboxylic acids; sulfones; sulfoxides; N,N-tetrasubstituted ureas; N-alkylated lactams or N-dialkylated acid amides; ethers; aliphatic, cycloaliphatic or aromatic hydrocarbons, which may be optionally substituted with F, Cl or $C_1$–$C_4$alkyl; carboxylic acid esters and lactones; nitrites; and glymes.

Some specific examples of solvents are: alcohols: methanol, ethanol, propanol, isopropanol, butanol, t-butanol, hexanol, heptanol, octanol, ethylene glycol and di-, tri- and tetra-ethylene glycol; ketones: acetone, methylethylketone, methylisobutylketone and cyclohexanone; carboxylic acids: ethanoic acid, propanoic acid and chloroacetic acid; sulfones: dimethylsulfone, diethylsulfone, tetramethylenesulfone and sulfolan; sulfoxides: dimethylsulfoxide; N,N-tetrasubstituted ureas: N-methylethyl-N'-methylethylurea, N-dimethyl-N'-dipropylurea, tetramethylurea, tetraethylurea, N,N'-dimethyl-N,N'-1,3-propyleneurea, N,N'-dimethyl-N,N'-ethyleneurea; N-alkylated lactams: N-methylpyrrolidone and N-ethylpyrrolidone; N-dialkylated acid amides: N-dimethylformamide, N-diethylformamide and N-dimethylacetamide; ethers: polyethylglycolether, di-,tri- and tetra-ethyleneglycoldimethylether, di-, tri- and tetra-ethyleneglycoldiethylether, terahydrofuran, dioxan, methyl-t-butylether, diethyleneglycolmonomethylether and ethyleneglycolmonomethylether; aliphatic hydrocarbons: methylene chloride, pentane and hexane; cycloaliphatic hydrocarbons: cyclohexane and decahydronaphthalene; aromatic hydrocarbons: xylene, tetrahydronaphthalene and dichlorobenzene; carboxylic acid esters: methyl benzoate, ethylacetate, λ-butyrolactone and n-butylacetate; nitrites: acetonitrile, benzonitrile and phenylacetonitrile; glymes: di-, tri- and tetra-glymes.

Step C) of the process according to the present invention and the production of the compounds of formula (6) are preferably conducted in the presence of a base which may be an organic base, an inorganic base or a mixture thereof and which is added prior to step B). The base is used as a buffer to neutralise mineral acid present during the formation of the diazonium salt reactants. The base may be used in at least equimolar amounts relative to the diazonium salt of formula (4) or (6) and preferably in an excess of up to 10 moles. Examples of suitable bases are Li-, Na-, K-, $NH_4$-, Mg-, Ca- and $NH(C_1$–$C_8alkyl)_3$-salts of carboxylic acids such as $C_1$–$C_4$carboxylic acids or benzoic acid. Specific examples of suitable bases are lithium-, potassium- or sodium acetate, -butyrate, -propionate and -stearate; barium- and calcium acetate; calcium propionate and -stearate; lithium- and sodium benzoate; ammonium acetate; and salts of acetic acid with triethylamine, tri-n-butylamine, tri-(2-ethylhexylamine), tri-n-octylamine and tri-n-dodecylamine. Preferred are alkaline metal acetates which form acetic acid as a desirable component in the arylafion step C). Particularly preferred bases are sodium and potassium acetate, and sodium and potassium bicarbonate, used in excess. The bases may also be used as salts in the catalyst generation, as described above.

Step C) of the process according to the present invention and the production of the compounds of formula (6) are preferably conducted at a temperature in the range of from −10 to 100° C., more preferably at a temperature in the range of from 0 to 80° C.

In addition to the avoidance of the direct handling of mutagenic benzidine reactants, the process of the present has the additional advantage that the same palladium catalyst can be used for both step C) of the process according to the present invention and for the production of the compounds of formula (6)

The following Examples further illustrate the present invention. Parts and percentages shown therein are by weight unless otherwise stated.

EXAMPLE 1

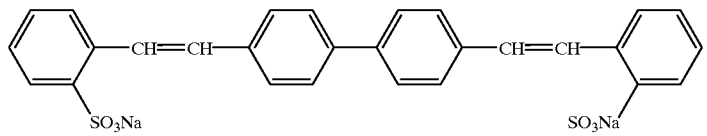

(101)

A) Preparation of the diazonium salt of 2-aminobenzenesulfonic acid

Into 150 g of anhydrous acetic acid, there are stirred 42 g of technical grade 2-aminobenzenesulfonic acid (38 g of 100% pure 2-aminobenzenesulfonic acid) and 3.8 g of conc. sulfuric acid (purity 96%), while keeping the reaction mixture at 15–20° C., by applying external cooling. At the same temperature, over 90 minutes, there are added 30.4 g of a 50% sodium nitrite solution. The reaction mixture is stirred for a further hour while the temperature is kept below 20° C. by cooling. Finally, the nitrite excess is determined and the necessary amount of 2-aminobenzene sulfonic acid is added to remove the excess.

B) Preparation of 2-styrenesulfonic acid 80 g of acetic anhydride are added, dropwise, over 3 hours to the reaction mixture obtained in part A). A weak exothermic reaction takes place. The reaction mixture is stirred for 1 hour, 36 g of anhydrous sodium acetate are added, the reaction mixture is stirred well until it becomes homogeneous and it is then transferred into a high pressure reactor. The reaction mixture is treated with 0.6 g of palladium[bis(dibenzalacetone)]$_2$ or with 0.6 g of a palladium chloride solution in hydrochloric acid (commercially available with 20% palladium content) and, after 5 minutes, the reactor is filled with an inert atmosphere of nitrogen. The pressure in the reactor is then increased to 50 bars by introducing ethylene and the reaction is conducted at 18–25° C. over 10 hours. The pressure of the mixture of ethylene and nitrogen is then reduced. There is obtained a whitish-grey suspension of the sodium salt of 2-styrenesulfonic acid in acetic acid. The evaluation of the degree of conversion of the diazo reactant is effected with an alkaline H-acid solution, for full conversion, no further violet coloured ring can be observed. The resulting suspension contains 43 g of the sodium salt of 2-styrenesulfonic acid and is used for the subsequent reaction step.

C) Rearrangement of hydrazobenzene 20 g of hydrazobenzene are dissolved in 150 g of glacial acetic acid. With stirring, the temperature is raised to the boil, held at the boil for 3 hours and then lowered to 20 to 30° C. The benzidine reaction suspension so obtained is subjected to diazofisation in the following step D).

D) Diazotisation of benzidine

To the stirred and cooled (to 0° C.) benzidine suspension obtained in step C), there are added, dropwise, over 20 minutes, 46 g of sodium nitrite as a 30% aqueous solution followed by 25 g of concentrated sulfuric acid, added over 20 minutes. During this time, the temperature is held at between 0 and 7° C. The reaction mass is then heated to 30° C. over 2 hours. Finally, the nitrite excess is determined and, if necessary, the excess is reduced by the addition of sulfamic acid.

E) Reaction of 2-styrenesulfonic acid with benzidinebisdiazo

To the reaction mass obtained in step D), there are added, dropwise, 20 g of acetic anhydride, the reaction mixture is neutralised with 37 g of sodium bicarbonate, the suspension of the sodium salt of 2-styrenesulfonic acid from step B) is introduced and then an additional 0.4 g of palladium[bis(dibenzalacetone)]$_2$ or 0.3 g of a palladium chloride solution in hydrochloric acid (commercially available with 20% palladium content) is stirred in. De-gasification immediately sets in. The reaction mixture is heated to 70° C. over 3 hours and stirred for a further 5 hours at this temperature.

The reaction mixture is worked up by firstly distilling off the acetic acid under vacuum. The residue obtained is dissolved in water, adjusted to 300 mls, heated to 90° C., treated with 2 g of activated carbon and the insoluble components are separated by filtration. Crystallisation of the reaction product from the filtered solution is induced by cooling the solution to 15° C. using a ramp. Finally, the product which crystallises out is separated by filtration, washed and dried. In this way, 40 g of the compound of formula (101) are obtained, representing a yield of 70% by weight, based on the weight of the hydrazobenzene used.

EXAMPLE 2

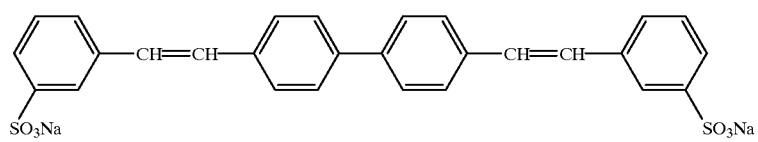

(102)

A) Preparation of the diazonium salt of 3-aminobenzenesulfonic acid

Into 100 g of water, there are stirred 43.3 g of 100% pure 3-aminobenzenesulfonic acid and 13.2 g of conc. sulfuric acid (purity 96%), while keeping the reaction mixture at 15–20° C., by applying external cooling. At the same temperature, over 60 minutes, there are added 34.5 g of a 50% sodium nitrite solution. The reaction mixture is stirred for a further 30 minutes while the temperature is kept below 20° C. by cooling. Finally, the nitrite excess is determined and the necessary amount of 3-aminobenzene sulfonic acid is added to remove the excess. The suspension is filtered with suction, washed with ice water and well stripped to obtain 50 g of an almost white filtercake.

B) Preparation of the sodium salt of 3-styrenesulfonic acid 30.6 g of acetic anhydride are added, dropwise, over 3 hours to the moist diazo presscake obtained in step B) in 200 ml of pentanol. A weak exothermic reaction takes place. The reaction mixture is stirred for 1 hour, 20.6 g of anhydrous sodium acetate are added, the reaction mixture is stirred well until it forms a suspension and it is then transferred into a high pressure reactor. The reaction mixture is treated with 0.6 g of palladium[bis(dibenzalacetone)]$_2$ and, after 5 minutes, the reactor is filled with an inert atmosphere of nitrogen. The pressure in the reactor is then increased to 50 bars by introducing ethylene and the reaction is conducted at 18–25° C. over 10 hours. The pressure of the mixture of ethylene and nitrogen is then reduced. There is obtained a whitish-grey suspension of the sodium salt of 3-styrenesulfonic acid in pentanollacetic acid. The evaluation of the degree of conversion of the diazo reactant is effected with an alkaline H-acid solution, for full conversion, no further violet coloured ring can be observed. The resulting suspension is used as such for the next reaction step.

C) Rearrangement of hydrazobenzene 20 g of hydrazobenzene are dissolved in 150 g of glacial acetic acid. With stirring and cooling, 25 g of methanesulfonic acid are added, dropwise, and the reaction temperature is held at 20 to 30° C. After stirring for a further hour, the benzidine reaction suspension so obtained is subjected to diazotisation in the following step D).

D) Diazotisation of benzidine

To the stirred and cooled (to 0° C.) benzidine suspension obtained in step C), there is added, dropwise, over 20 minutes, 46 g of sodium nitrite as a 30% aqueous solution. During this time, the temperature is held at between 0 and 7° C. The reaction mass is then heated to 30° C. over 2 hours. Finally, the nitrite excess is determined and, if necessary, the excess is reduced by the addition of sulfamic acid.

E) Reaction of 3-styrenesulfonic acid with benzidinebisdiazo

To the reaction mass obtained in step D), there are added, dropwise, 20 g of acetic anhydride, the reaction mixture is neutralised with 37 g of sodium bicarbonate, the suspension of the sodium salt of 3-styrenesulfonic acid from step B) is introduced and then an additional 0.4 g of palladium[bis (dibenzalacetone)]$_2$ is stirred in. De-gasification immediately sets in. The reaction mixture is heated to 70° C. over 3 hours and stirred for a further 5 hours at this temperature.

The reaction mixture is worked up by firstly distilling off the acetic acid under vacuum. The residue obtained is dispersed in 400 mls of water, heated to 90° C., the insoluble components are separated by filtration and washed. The moist filtercake is dissolved in a mixture of dimethylformamide and water at 100° C., treated with 2 g of activated carbon and then clarified. Crystallisation of the reaction product from the filtered solution is induced by cooling the solution to 15° C. using a ramp. Finally, the product which crystallises out is separated by filtration, washed and dried. In this way, 42 g of the compound of formula (102) are obtained, representing a yield of 75% by weight, based on the weight of the hydrazobenzene used.

We claim:

1. A process for the production of a compound of formula:

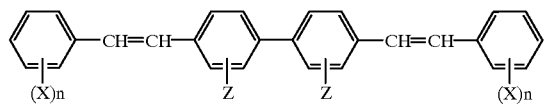

(1)

in which X is hydrogen, halogen, $NO_2$, $CF_3$, CN, $C_1$–$C_4$alkyl, $C_1$–$C_4$alkoxy, COO—$C_1$–$C_4$alkyl, CO—$C_1$–$C_4$alkyl, NH-($C_1$–$C_4$alkyl), N($C_1$–$C_4$alkyl)$_2$, NH($C_1$–$C_4$alkyl-OH), N($C_1$–$C_4$alkyl-OH)$_2$, COOH or $SO_3H$ or an ester or amide thereof, or COOM or $SO_3M$ in which M is Na, K, Ca, Mg, ammonium, mono-, di-, tri- or tetra-$C_1$–$C_4$alkylammonium, mono-, di- or tri-hydroxyalkylammonium or ammonium that is di- or tri-substituted with a mixture of $C_1$–$C_4$alkyl and $C_1$–$C_4$hydroxyalkyl groups;

Z is hydrogen, $C_1$–$C_4$alkyl, $C_1$–$C_4$alkoxy, $CF_3$, halogen (F, Cl, Br, I), $SO_3H$ or $SO_3M$ in which M has its previous significance; and n is 1 or 2; comprising A) rearranging a hydrazobenzene compound having the formula:

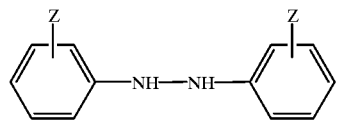

(2)

in which Z has its previous significance, to produce in situ a compound having the formula:

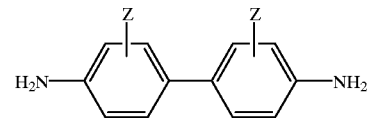

(3)

B) diazotising the compound of formula (3) to produce a compound having the formula:

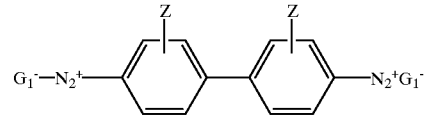

(4)

in which Z has its previous significance and $G_1$ is a counter ion; and

C) reacting the compound of formula (4) with 2 moles of a compound having the formula:

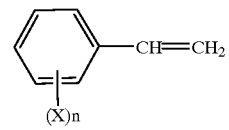

(5)

in which X and n have their previous significance, in the presence of an inorganic or organic palladium salt, or a mixture thereof, as catalyst-precursor, to produce a compound having the formula (1).

2. A process according to claim 1 in which step C) of the process is conducted without the intermediate isolation of the reactant of formula (4) obtained in step B).

3. A process as claimed in claim 1 in which in the compounds of formula (1) and (5), n is 1 and X is hydrogen, cyano, COOM or $SO_3M$ in which M is as defined in claim 1 and, in the compounds of formula (1), (2), (3) and (4), Z is hydrogen.

4. A process according to claim 1 in which in the compounds of formula (4), $G_1$ is $H_2PO_4^-$, $HPO_4^{2-}$, $NO_3^-$, $CF_3COO^-$, $^-OOC-COO^-$ (oxalate), $Cl_3CCOO^-$, $ClCH_2COO^-$, $I^-$, $Cl^-$, $Br^-$, $F^-$, $ClO_4^-$, $PF_6^-$, $BF_4^-$, $Oac^-$, $HSO_4^-$, $SO_4^{2-}$, $CH_3(C_6H_4)SO_3^-$ or $CH_3SO_3^-$.

5. A process according to claim 1 which additionally comprises preparing the compound of formula (5) used in step C) by reacting a diazonium compound having the formula:

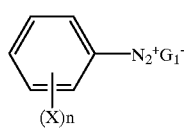

(6)

in which X, n and $G_1$ are as defined in claim 1, with ethylene in the presence of an inorganic or organic palladium salt, or a mixture thereof, as catalyst-precursor, to produce the compound having the formula (5).

6. A process according to claim 5 in which n is 1 and the amino component precursor of the diazo salt starting material of formula (6) is aniline, 2-, 3- or 4-chloro-aniline, 2-, 3- or 4-bromo-aniline, 2-, 3- or 4-iodo-aniline, 2-, 3- or 4-trifluoromethyl-aniline, 2-, 3- or 4-nitrilo-aniline, 2-, 3- or 4-methyl-aniline, 2-, 3- or 4-ethyl-aniline, 2-, 3- or 4-n-propyl-aniline, 2-, 3- or 4-n-butyl-aniline, 2-, 3- or 4methoxy-aniline, 2-, 3- or 4-ethoxy-aniliner 2-, 3- or 4-n-propoxy-aniline, 2-, 3- or 4-n-butoxy-aniline, 2-, 3- or 4-amino-benzoic acid or its methyl, -ethyl-, n-propyl or n-butyl ester, 2-, 3- or 4amino-acetophenone, 2-, 3- or 4-methylamino-aniline, 2-, 3- or 4-ethylamino-aniline, 2-, 3- or 4-hydroxyethyleneamino-aniline, 2-, 3- or 4-di(hydroxyethyleneamino)-aniline or 2-, 3- or 4-aminobenzene sulfonic acid.

7. A process according to claim 5 in which n is 2 and the amino component precursor of the diazo salt starting material of formula (6) is 3- or 4-aminobenzo-1,2-dinitrile, 3- or 4-aminobenzene-1,2-dicarboxylic acid or its dimethyl, -diethyl-, di-n-propyl or di-n-butyl ester, aminobenzene-2,4-disulfonic acid, aminobenzene-3,5-disulfonic acid or aminobenzene-2,5-disulfonic acid.

8. A process according to claim 6 in which the amino component precursor of the diazonium compound of formula (6) is 2-, 3- or 4-aminobenzene sulfonic acid.

9. A process according to claim 1 in which the product of the process has the formula:

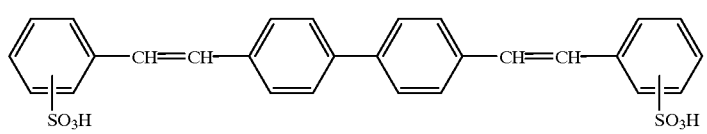

(101)

or an alkali metal salt.

10. A process according to claim 9 in which the alkali metal salt is the sodium salt.

11. A process according to claim 5 in which the palladium catalyst precursor, used in step C) and in the production of the compounds of formula (6), is generated, in situ or ex situ, by reduction of a palladium (11) compound, optionally in the presence of a salt, and optionally in the presence of a suitable ligand-forming or colloid-stabilising compound.

12. A process according to claim 11 in which the palladium (II) compound is $PdCl_2$, $PdBr_2$, $Pd(NO_3)_2$, $H_2PdCl_4$, $Pd(OOCCH_3)_2$, $[PdCl_4]Na_2$, $[PdCl_4]Li_2$, $[PdCl_4]K_2$, palladium(ll)acetylacetonate, dichloro-(1,5-cyclooctadiene) palladium(II), dichlorobis-(acetonitrile)palladium(II), dichlorobis-(benzonitrile)palladium(ll), 7-allylpalladium(ll) chloride dimer, bis-(π-methallyl palladium(II)chloride) or π-allylpalladium(II)acetylacetonate.

13. A process according to claim 11 in which the salt is sodium acetate.

14. A process according to claim 11 in which the ligand-forming compound is an olefin having the formula $CHR_2=CHR_3$ in which $R_2$ is H, F, Cl, Br or $-COOR_4$, and $R_3$ is $-COO(C_1-C_4alkyl)$, $-COR_4$ or $C_1-C_2alkyl$ optionally substituted by halogen; dibenzylideneacetone optionally substituted in the benzene rings with F, Cl or Br, $SO_3M$ in which M is Na, K, Ca, Mg, ammonium, mono-, di-, tri- or tetra-$C_1-C_4$ alkylammonium, mono-, di- or tri-hydroxyalkylammonium or ammonium that is di- or tri-substituted with a mixture of $C_1-C_4alkyl$ and $C_1-C_4hydroxyalkyl$ groups, $C_1-C_4alkyl$ or $C_1-C_4alkoxy$; a phosphite of the formula $P(OR_5)$ in which $R_5$ is phenyl, $C_1-C_6alkyl$ or a partially or perfluorinated $C_1-C_6alkyl$; or CO.

15. A process according to claim 11 in which the reduction is effected using, as a reducing agent, CO, $H_2$, a formate, a primary or secondary $C_1-C_8alkanol$, hydrazine, an amine, a mixture of CO with an alkanol or water, or the ligating olefin per se.

16. A process according to claim 12 in which the catalyst is added as $Pd(dba)_2$, $Pd(dba)_3 \cdot solvent$ $Pd_2(dba)_3$ or $Pd_2(dba)_3 \cdot solvent$.

17. A process according to claim 12 in which the palladium catalyst is used in an amount of 0.01 to 5 mole %, based on the diazonium salt of formula (4) or the styrene compound of formula (5).

18. A process according to claim 5 in which step C) and the production of the compounds of formula (6) is conducted in water, an organic solvent or a two-phase solvent system comprising water and a water-insoluble organic solvent.

19. A process according to claim 18 in which the organic solvent is in one or more of an alcohol; ketone; carboxylic acid; sulfone; sulfoxide; N,N-tetrasubstituted urea; N-alkylated lactam or N-diakkylated acid amide; ether; aliphatic, cycloaliphatic or aromatic hydrocarbon, which may be optionally substituted with F, Cl or $C_1-C_4alkyl$; carboxylic acid ester or lactone; nitrile; and a glymd.

20. A process according to claim 5, in which step C) and the production of the compounds of formula (6) is conducted in the presence of an organic base, an inorganic base or a mixture thereof which is added prior to step C).

21. A process according to claim 20 in which the base is used in an excess of up to 10 moles relative to the diazonium salt.

22. A process according to claim 20 in which the base is a Li-, Na-, K-, $NH_4$-, Mg-, Ca- or $NH(C_1-C_{18}alkyl)_3$-salt of a carboxylic acid.

23. A process according to claim 22 in which the base is lithium-, potassium- or sodium acetate, -butyrate, -propionate or -stearate; barium- or calcium acetate; calcium propionate or -stearate; lithium- or sodium benzoate; ammonium acetate; or a salt of acetic acid with triethylamine, tri-n-butylamine, tri-(2-ethylhexylamine), tri-n-octylamine or tri-n-dodecylamine.

24. A process according to claim 23 in which the base is an alkaline metal acetate which forms acetic acid as a component in the diazotization step B).

25. A process according to claim 24 in which the base is sodium or potassium acetate, or sodium or potassium bicarbonate, used in excess.

26. A process according to claim 1 in which step C) is conducted at a temperature in the range of from −10 to 100° C.

27. A process according to claim 26 in which the process is conducted at a temperature in the range of from 0 to 80° C.

* * * * *